US006303790B1

(12) United States Patent
Hilpert et al.

(10) Patent No.: US 6,303,790 B1
(45) Date of Patent: Oct. 16, 2001

(54) PROCESS FOR THE PREPARATION OF PYRIDINE DERIVATIVES

(75) Inventors: Hans Hilpert, Reinach; Fabienne Hoffmann-Emery, Birsfelden, both of (CH); Goesta Rimmler, Bad Krozingen (DE); Mark Rogers-Evans, Ettingen (CH); Helmut Werner Stahr, Lörrach (DE); Pius Waldmeier, Wegenstetten (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/716,538

(22) Filed: Nov. 20, 2000

(30) Foreign Application Priority Data

Nov. 29, 1999 (EP) .................................................. 99123686

(51) Int. Cl.[7] ...................... C07D 213/75; C07D 213/82

(52) U.S. Cl. ........................ 546/308; 546/316; 544/124; 544/360

(58) Field of Search ...................................... 546/308, 316; 544/124, 360

(56) References Cited

FOREIGN PATENT DOCUMENTS 0 235 663    9/1987   (EP) .
1035115      9/2000   (EP) .

OTHER PUBLICATIONS

W. Schlecker, et al., Tetrahedron vol. 51, No. 35, (1995) pp. 9531–9542.

*Primary Examiner*—Zinna Northington Davis
(74) *Attorney, Agent, or Firm*—George W. Johnston; Patricia S. Rocha-Tramaloni; Eileen M. Ebel

(57) ABSTRACT

A process is described for preparing certain 4-alkyl- or 4-aryl-pyridine derivatives.

14 Claims, No Drawings

PROCESS FOR THE PREPARATION OF PYRIDINE DERIVATIVES

FIELD OF THE INVENTION

The present invention relates to a method of preparing 4-alkyl- or 4-aryl-pyridine derivatives.

BACKGROUND OF THE INVENTION

It is known that certain 4-phenyl-pyridine derivatives can be prepared by the method disclosed in EP1035115.

SUMMARY OF THE INVENTION

The present invention relates to a process for preparing a compound of formula

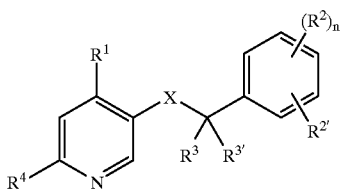

I wherein
- $R^1$ is lower alkyl or aryl, optionally substituted by lower alkyl, lower alkoxy, halogen or trifluoromethyl;
- $R^2$ and $R^{2'}$ are independently from each other hydrogen, halogen, trifluoromethyl, lower alkoxy or cyano; or
- $R^2$ and $R^{2'}$ may together be —CH=CH—CH=CH— and form a fused ring with the carbon atoms to which they are attached, optionally substituted by lower alkyl or lower alkoxy;
- $R^3/R^{3'}$ are independently from each other hydrogen, lower alkyl, or taken together with the carbon atom to which they are attached, form a cycloalkyl group;
- $R^4$ is hydrogen, lower alkyl, —N(R$^5$)$_2$, —N(R$^5$)(CH$_2$)$_n$OH, —N(R$^5$)S(O)$_2$-phenyl, —N(R$^5$)S(O)$_2$-lower alkyl, —N=CH—N(R$^5$)$_2$, —N(R$^5$)C(O)R$^5$ or a cyclic tertiary amine of the group

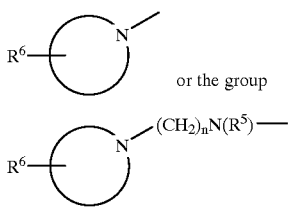

or the group

- $R^5$ is hydrogen, lower alkyl, or benzyl, which is optionally substituted by lower alkyl;
- $R^6$ is hydrogen, hydroxy, lower alkyl, —(CH$_2$)$_n$COO-lower alkyl, —N(R$^5$)CO-lower alkyl, hydroxy-lower alkyl, cyano, —(CH$_2$)$_n$O(CH$_2$)$_n$OH, —CHO, or a 5-or 6 membered heterocyclic ring, optionally bonded via an alkylene group,
- X is —C(O)N(R$^5$)— or —N(R$^5$)C(O)—;
- n is 0–4; and pharmaceutically acceptable acid addition salts thereof, which process comprises a) reacting a compound of formula

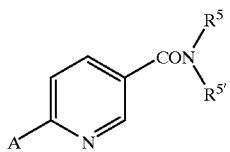

IV-1 wherein A denotes R or $R^4$, and R is halogen, and $R^{5'}$ has the same meaning as $R^5$, wherein $R^5$ and $R^{5'}$ may be independent from each other, with a compound of formula R$^1$MgHal    V wherein Hal is a halogen atom,
to a mixture of compounds of formulae

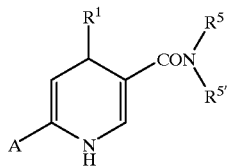

X-1 and

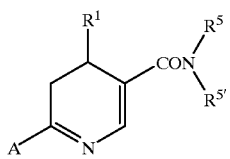

XI-1 or a') reacting a compound of formula IV-1, wherein A is R, with a compound of formula V and with a compound of formula

HR$^4$    VII in one reaction step, to a compound of formula

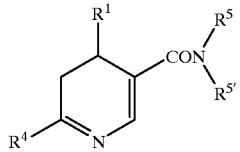

VI and b) oxidizing a compound of formulae X-1, XI-1 or VI with an oxidizing agent, to a compound of formula

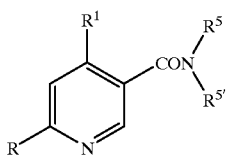
XII or

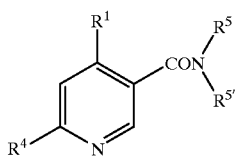
VIII and c) reacting a compound of formula VIII with a compound of formula

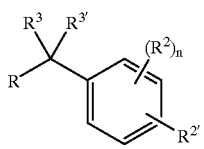
IX wherein R is halogen, to a compound of formula

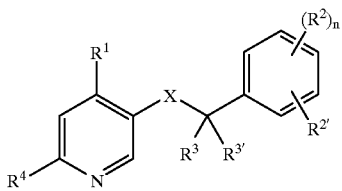
I wherein X is —CON(R⁵)—, or c'i) reacting a compound of formula VIII with a compound of formula IX, to a compound of formula

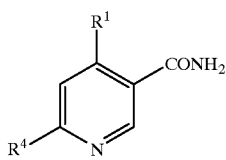
XIII and ii) reacting a compound of formula XIII to a compound of formula

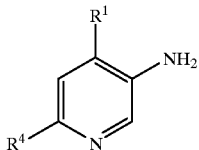
XIV or

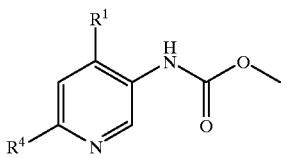
XV and iii) transforming a compound of formulae XIV or XV to a compound of formula

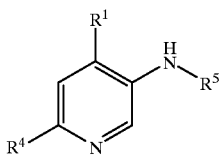
XVI wherein $R^5$ is methyl, and iv) reacting a compound of formula XVI with a compound of formula

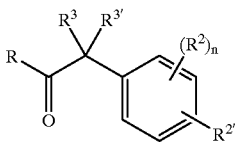
XVII to a compound of formula

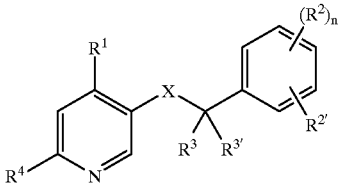
I wherein X is —N(R⁵)C(O)—.

DETAILED DESCRIPTION OF THE INVENTION

The present invention relates to a process for the preparation of compounds of the general formula

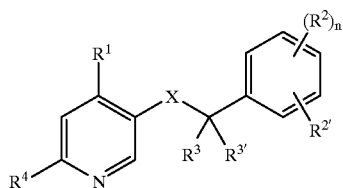

wherein
R¹ is lower alkyl or aryl, optionally substituted by lower alkyl, lower alkoxy, halogen or trifluoromethyl;
R² and R²' are independently from each other hydrogen, halogen, trifluoromethyl, lower alkoxy or cyano; or
R² and R²' may together be —CH=CH—CH=CH— and form a fused ring with the carbon atoms to which they are attached, optionally substituted by lower alkyl or lower alkoxy;
R³/R³' are independently from each other hydrogen, lower alkyl, or taken together with the carbon atom to which they are attached, form a cycloalkyl group;
R⁴ is hydrogen, lower alkyl, —N(R⁵)₂, —N(R⁵)(CH₂)ₙOH, —N(R⁵)S(O)₂-phenyl, —N(R⁵)S(O)₂-lower alkyl, —N=CH—N(R⁵)₂, —N(R⁵)C(O)R⁵ or a cyclic tertiary amine of the group

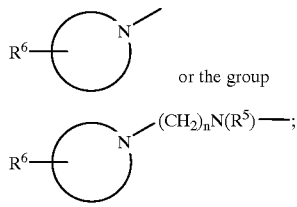

R⁵ is hydrogen, lower alkyl, or benzyl, which is optionally substituted by lower alkyl;
R⁶ is hydrogen, hydroxy, lower alkyl, —(CH₂)ₙCOO-lower alkyl, —N(R⁵)CO-lower alkyl, hydroxy-lower alkyl, cyano, —(CH₂)ₙO(CH₂)ₙOH, —CHO, or a 5- or 6-membered heterocyclic ring, optionally bonded via an alkylene group,
X is —C(O)N(R⁵)— or —N(R⁵)C(O)—;
n is 0–4;
and to pharmaceutically acceptable acid addition salts thereof.

The compounds of formula I and their salts are characterized by valuable therapeutic properties. It has been found that compounds of formula I are antagonists of the Neurokinin 1 (NK-1, substance P) receptor.

The most preferred indications are those which include disorders of the central nervous system, for example the treatment or prevention of certain depressive disorders, anxiety or emesis by the administration of NK-1 receptor antagonists.

The following definitions of the general terms used in the present description apply irrespective of whether the terms in question appear alone or in combination.

As used herein, the term "lower alkyl" denotes a straight- or branched-chain alkyl group containing from 1–10 carbon atoms, for example, methyl, ethyl, propyl, isopropyl, n-butyl, i-butyl, t-butyl and the like. Preferred lower alkyl groups are groups with 1–4 carbon atoms.

The term "lower alkoxy" denotes a group wherein the alkyl residue is as defined above, and which is attached via an oxygen atom.

The term "halogen" denotes fluorine, chlorine, bromine and iodine.

The term "cycloalkyl" denotes a saturated carbocyclic group (e.g., a nonaromatic ring), containing 3–6 carbon atoms (i.e., $C_3$–$C_6$ cycloalkyl).

A "cyclic tertiary amine" denotes a ring system which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine, which ring is directly attached via the ring nitrogen to the remainder of the molecule or is attached through the linker —(CH₂)ₙN(R⁵)—. The cyclic tertiary amine may contain three to five carbon atoms. When the ring is substituted it is preferably substituted at the heteroatom, for example N-alkyl-piperazine. Examples of such rings include pyrrol-1-yl, imidazol-1-yl, piperidin-1-yl, piperazin-1-yl, which is optionally substituted by lower alkyl, morpholin-4-yl, thiomorpholin-4-yl; 1-oxo-thiomorpholin-4-yl or 1,1-dioxo-thiomorpholin-4-yl. Preferred cyclic tertiary amines are the piperazinyl and the morpholinyl groups.

The term "aryl" means a monocyclic or bicyclic aromatic ring, such as phenyl, benzyl, naphthyl and the like. Preferred is the phenyl group.

The term a "5–6 membered hetercyclic ring" is a ring system which contains from 1 to 4 heteroatoms, selected form the group consisting of oxygen, nitrogen, and sulfur, and with one of the carbon atoms in said ring being unsubstituted or substituted with an oxo group. Examples of such rings are pyrimidine, oxadiazole, triazole, tetrazole, pyridine, thiazole, thiene, furane, pyrane, pyrrole, imidazole, pyrazole, isothiazole, piperazine or piperidine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The present compounds of formula I and their pharmaceutically acceptable salts can be prepared by methods described in or analogous to those in EP1035115, for example, by processes described in schemes 1 and 2 below:

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-diisopropylethyl-amine |
| KHMDS | potassium hexamethyldisilazide |

Scheme 1

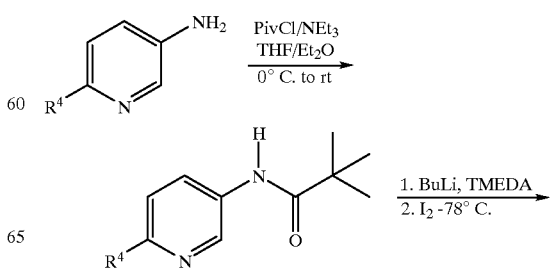

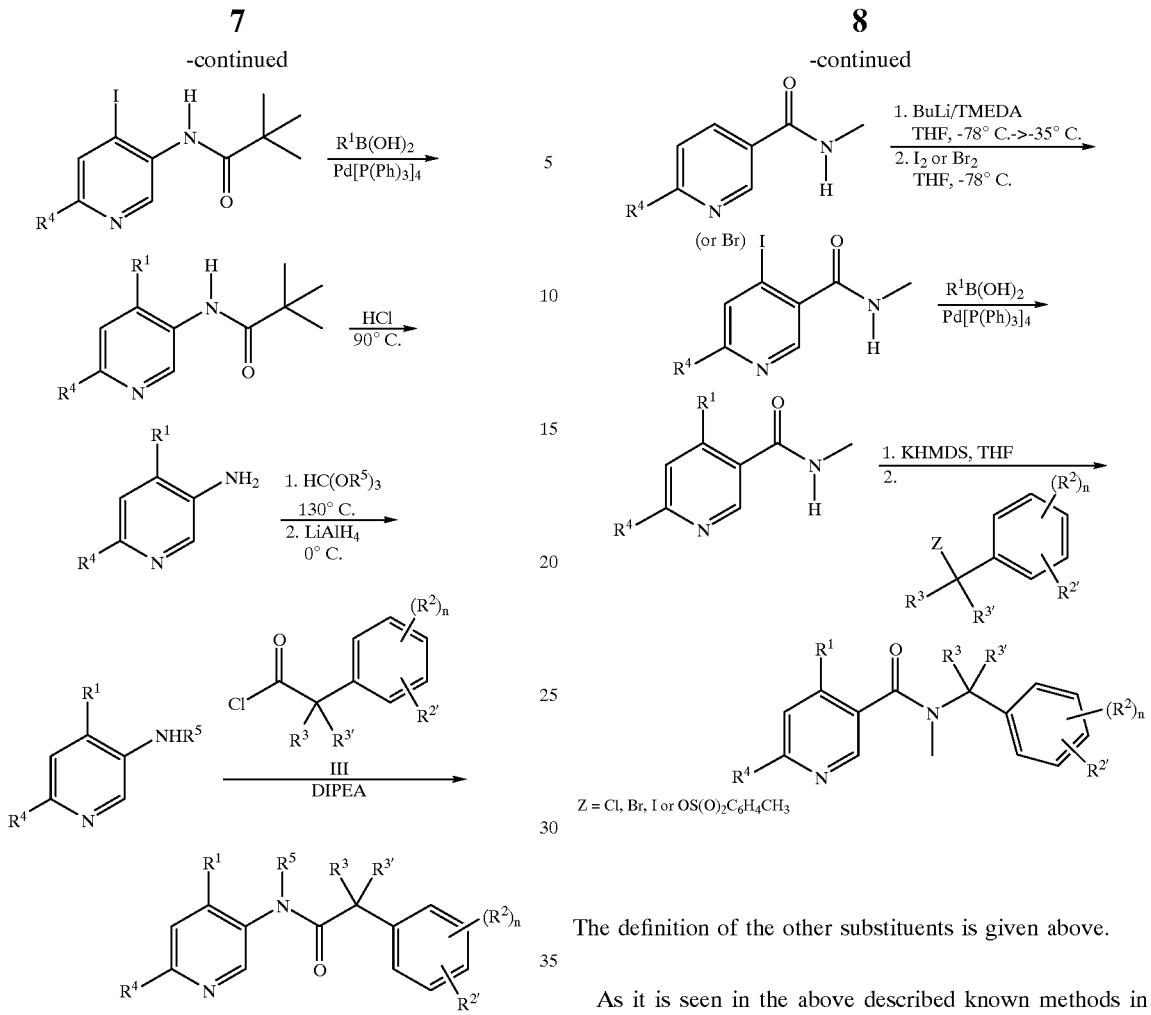

wherein the definition of substituents is given above.

Scheme 2

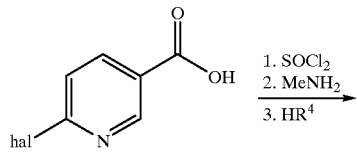

The definition of the other substituents is given above.

As it is seen in the above described known methods in schemes 1 and 2, the introduction of the group $R^1$, which may be lower alkyl or optionally substituted aryl, is carried out with an activated pyridine ring, wherein the activating group is a halogen atom, such as bromo or iodo.

Now, it has surprisingly been found that the preparation of compounds of formula I may be carried out in accordance with the processes, described below in schemes 3 and 4.

The starting compound of formula II or the other starting materials (III, V and VII) are known compounds or may be prepared by known methods.

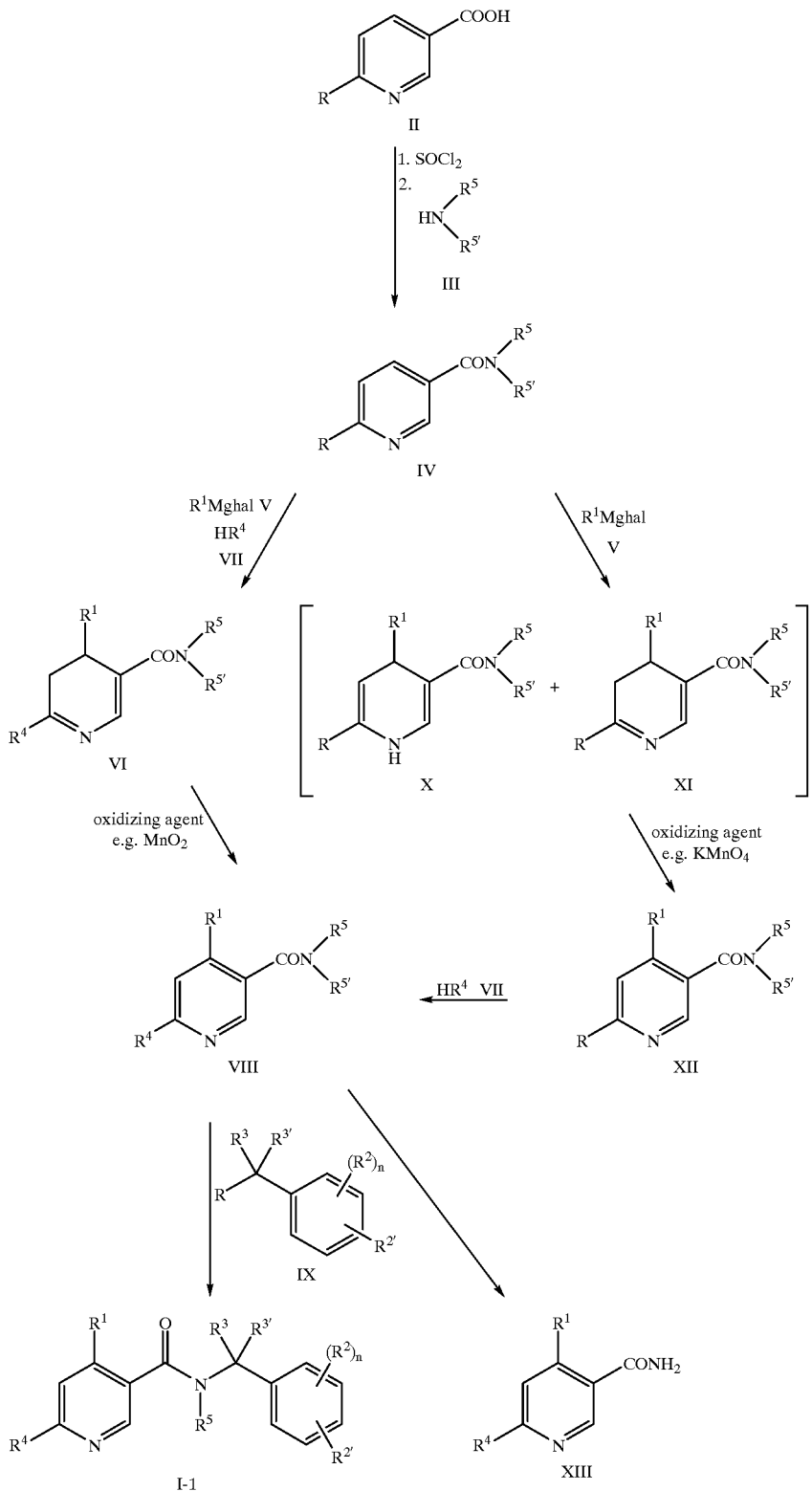
Scheme 3

Scheme 4

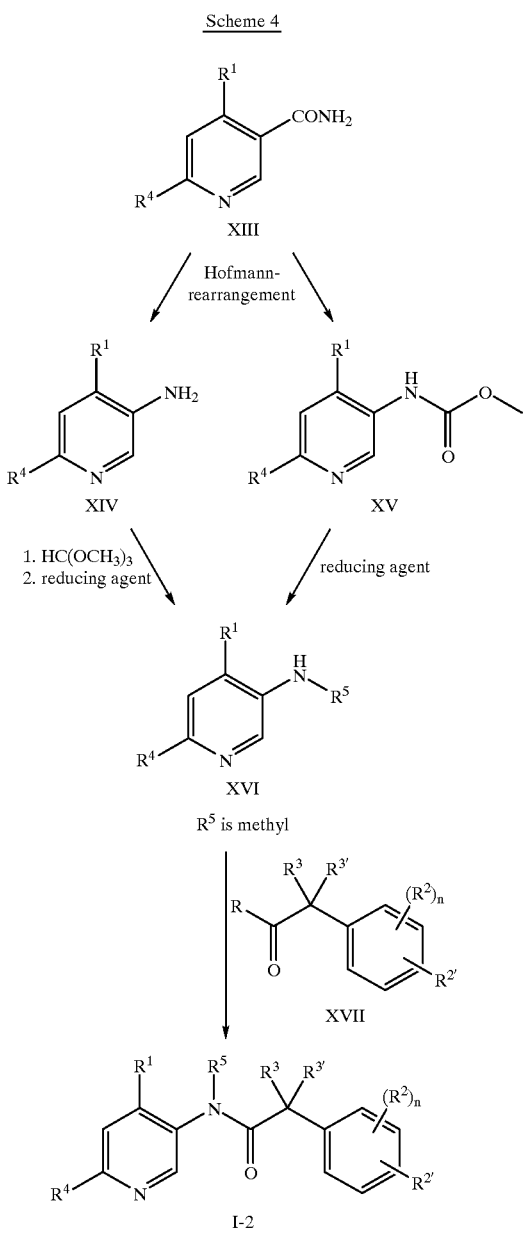

In schemes 3 and 4 the definition of substituents for $R^1$, $R^2$, $R^{2'}$, $R^3$, $R^{3'}$, $R^4$ and $R^5$ is described above and $R^{5'}$ in scheme 3 has the same meaning as $R^5$, wherein $R^5$ and $R^{5'}$ may be independent from each other. R is a halogen atom, preferably chloro.

It has been found that the preparation of compounds of formula I may be carried out via an introduction of the group $R^1$ in a compound of formula

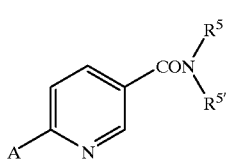

IV-1 in the 4-position of the pyridine ring via an 1,4-addition without activation of the pyridine ring.

In formula IV-1 A denotes the group R or $R^4$, wherein R is a halogen atom, preferably chloro and $R^4$, $R^5$ and $R^{5'}$ have the significances given above.

In accordance with the invention, a corresponding compound of formula IV-1, wherein A is $R^4$ or R, is treated with a compound of formula

$R^1MgHal$     V wherein $R^1$ is lower alkyl or aryl, optionally substituted by lower alkyl, lower alkoxy, halogen or trifluoromethyl and Hal is a halogen atom, preferably chloro, to give a mixture of compounds of formulae

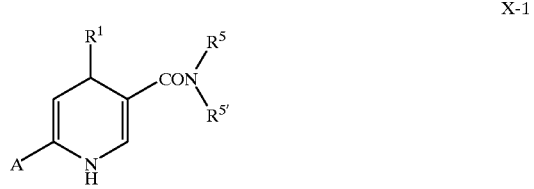

X-1 and

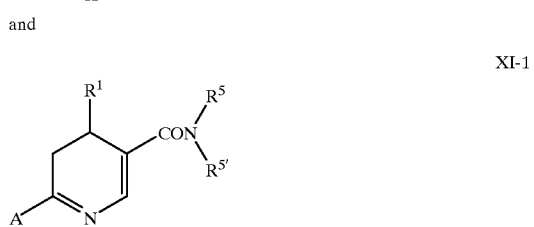

XI-1 or, alternatively, a compound of formula IV-1, wherein A is R, is treated with a compound of formula V and with a compound of formula

$HR^4$     VII in the same reaction step to give a compound of formula

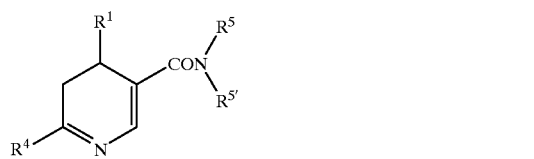

VI wherein $R^4$ has the significances given above.

It has been shown that the introduction of the group $R^1$ occurs selectively in the 4-position of the pyridine ring without an activation of the pyridine ring on this position or on the nitrogen atom. This unexpected reaction is carried out in a solvent, such as ethers, preferably tetrahydrofuran (THF). The reaction temperature is about 20–60° C., preferably 20–40° C.

After stirring the reaction mixture for about 1–16 hours a compound of formula X-1 and XI-1 is obtained in good yields.

If the introduction of the group $R^1$ and the replacement of the group R by $R^4$ occurs in the same reaction step, compounds of formula VI are obtained.

If A denotes a halogen atom, this atom may be replaced by the group $R^4$ in conventional manner by reaction with a compound of formula VII, for example with $HN(R^5)_2$, $HN(R^5)(CH_2)_nOH$, $HN(R^5)S(O)_2$-phenyl, $HN(R^5)S(O)_2$-lower alkyl, $HN=CH-N(R^5)_2$, $HN(R^5)C(O)R^5$ or a cyclic tertiary amine of the group

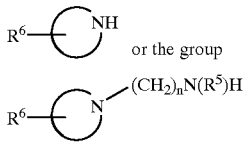

or the group wherein the definition of substituents is given above.

If the reaction is carried out in a solvent, suitable solvents are toluene, THF or EtOAc. The reaction is carried out at a temperature of about 60–100° C. The preferred temperature is 100° C.

The compounds of formulae X-1 and XI-1 or VI are then oxidized with an oxidizing agent, such as $Mn(OAc)_3$, $Cu(OAc)_2$, iodine, bromine, N-bromosuccinimide, Pd/C, Pt/C, DDQ (2,3-dichloro-5,6-dicyano-1,4-benzoquinone), o-chloranil, $H_2O_2$-urea, $Na_2CO_3$—$H_2O_2$, $MnO_2$, $KMnO_4$, $RuCl_2(PPh_3)_3$Cer(IV)ammoniumnitrate, $HNO_3$ or S in conventional manner to give a compound of formula

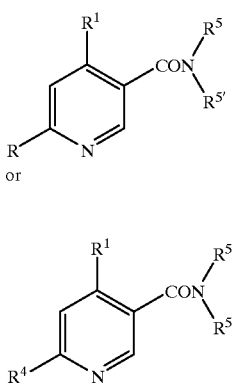

XII or

VIII wherein the definition of substituents is described above.

The preferred oxidizing agents are $Mn(OAc)_3$, $Cu(OAc)_2$, iodine, DDQ, o-chloranil, $MnO_2$, or $KMnO_4$. The oxidation is carried out in conventional manner at a temperature between –100° C. and 140° C., preferably between –60° C. and 40 ° C.

If desired, a compound of formula XII can be reacted with a compound of formula VII, to a compound of formula VIII.

The replacement of the group R (halogen) by $R^4$ may occur in any step of the reaction thus far.

The obtained compound of formula VIII is then reacted with a compound of formula

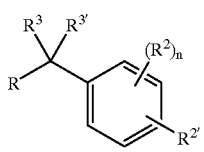

IX wherein $R^2$ and $R^{2'}$ are independently from each other hydrogen, halogen, lower alkoxy, trifluoromethyl or cyano, R is halogen, preferably chloro or bromo, and $R^3/R^{3'}$ is independently from each other hydrogen, lower alkyl or form together a cycloalkyl group, in a solvent, such as THF and in the presence of potassium bis(trimethylsilyl)amide, to give a compound of formula

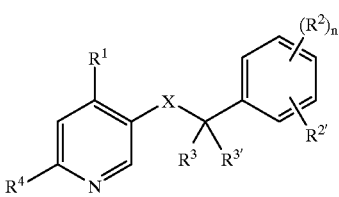

I wherein X is —$CON(R^5)$—, and the definition of the other substituents is given above.

A preferred compound, which has been prepared as described above, is N-(3,5-bis-trifluoromethyl-benzyl)-N-methyl-6-(4-methyl-piperazin-1-yl)-4-o-tolyl-nicotinamide.

For the preparation of a compound of formula I, wherein X is —$N(R^5)C(O)$—, a compound of formula VIII is transformed to a compound of formula

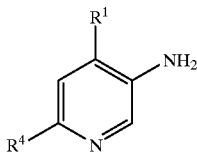

XIII in the presence of $CH_3SO_3H$ or AcOH and $H_2SO_4$ at about 100° C., and, subsequently, the amino substituent is introduced via a Hofmann rearrangement to a compound of formula

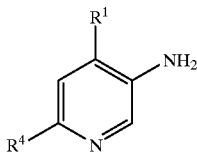

XIV or to the corresponding methylcarbamate of formula

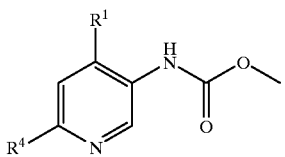

XV with an oxidizing agent such as hypohalite, N-halosuccinimide or a hypervalent iodobenzene, for example sodium hypochlorite, N-bromosuccinimide or iodobenzene diacetate, in the presence of a base, for example NaOH or $CH_3ONa$. The reaction is carried out in water or an organic solvent, such as an alcohol, dichloromethane, THF or dioxane at a temperature of about –10 to 40° C. for the preparation of the compound of formula XV and at a temperature of about 20–80° C. for the preparation of the compound of formula XIV.

A compound of formula XIV is further transformed to a compound of formula

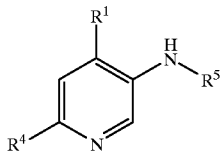

XVI wherein $R^5$ is methyl, by treatment with an alkyl orthoformate and a catalytic amount of an acid, for example with $HC(OCH_3)_3$ and trifluoro acetic acid, followed by reduction with $LiAlH_4$, $NaBH_4$, $BH_3$—THF or Red-Al®, preferably $BH_3$—THF or $LiAlH_4$.

A compound of formula XV is further transformed to a compound of formula XVI by reduction with $LiAlH_4$, preferably Red-Al®.

The last step for the preparation of a compound of formula I is the reaction of a compound of formula XVI with a compound of formula

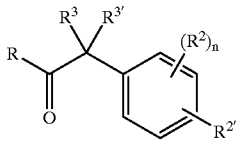

XVII in the presence of a base, for example a tertiary amine at a temperature of about 0–50° C., to give a compound of formula

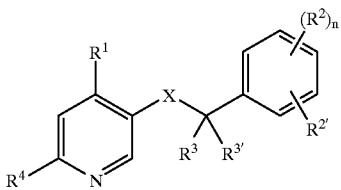

I wherein X is —$N(R^5)C(O)$— and the definition of the other substituents is given above.

A preferred compound, obtained in the above described process, is 2-(3,5-bis-trifluoromethyl-phenyl)-N-methyl-N-(6-morpholin-4-yl-4-o-tolyl-pyridin-3-yl)-isobutyramide.

In the following Examples the invention is described in more detail.

EXAMPLE I

N-(3,5-Bis-trifluoromethyl-benzyl)-N-methyl-6-(4-methyl-piperazin-1-yl)-4-o-tolyl-nicotinamide a) Chloro-N-methyl-nicotinamide To a mixture of 63.0 g (0.40 mol) 6-chloronicotinic acid and 37.7 ml (0.52 mol) thionylchloride was added 340 ml toluene and 0.92 ml (12.0 mmol) DMF. The brown suspension was heated to 95° C. and stirred at 95° C. for 1.5 h. The solvent was subsequently removed and the residue treated with 340 ml $CH_2Cl_2$. This solution was cooled to 2° C. and treated with 81.0 g (1.2 mol) methylaminhydrochloride. To the so formed brown suspensions was added at −2° C. to −6° C. dropwise over 75 min 167.5 ml (1.2 mol) $NEt_3$ (the reaction was finished after further 30 min.). The reaction mixture was poured onto 400 ml brine and 100 ml sat. aqueous sodium carbonate and extracted. The aqueous phase was extracted with total 2.4 l $CH_2Cl_2$. The organic phases were washed with 400 ml sat. aqueous sodium carbonate and 400 ml brine, combined, dried over $MgSO_4$. The solvent was removed under reduced pressure to give 67.5 g (98.9%) product as brown crystals, m.p. 147.5–148.0° C.

MS (EI): m/e=172 (13), 171 (18), 170 ([M] 37), 169 (47), 142 (34), 140 (100), 135 (67), 112 (43).

b) (RS)-6-(4-Methyl-piperazin-1-yl)4-o-tolyl-4,5-dihydro-pyridine-3-carboxylic acid methylamide A solution of 3.0 g (17.6 mmol) 6-chloro-N-methyl-nicotinamide in 42.0 ml THF was treated at 4° C. dropwise over 15 min. with 43.8 ml (43.8 mmol) o-tolylmagnesiumchloride-solution (1M in THF). The reaction mixture was stirred for 2 h at r.t., cooled to 0° C. and treated dropwise with 50 ml 5% aqueous $NH_4Cl$. The aqueous phase was separated and extracted twice with toluene and the organic phases were washed twice with 5% aqueous $NH_4Cl$. The combined organic phases were dried over $Na_2SO_4$ and filtrated. The filtrate was treated with 9.8 ml (88.3 mmol) 1-methylpiperazine and stirred for 1.5 h at r.t. The reaction mixture was treated with 40 ml 5% aqueous $NH_4Cl$ and the pH adjusted with NaOH (28%) to 10. The aqueous phase was separated and extracted twice with $CH_2Cl_2$ and the organic phases were washed twice with brine. The combined organic phases were dried over $Na_2SO_4$ and filtrated. The solvent was removed under reduced pressure to yield 5.4 g (94.6 %) product as yellowish crystals, m.p. 137.0–138.0° C.

MS (ISP): m/e=328 (24), 327 ([M+H$^+$] 100), 270 (12).

c) N-Methyl-6-(4-methyl-piperazin-1-yl)-4-o-tolyl-nicotinamide

A solution of 1.5 g (4.6 mmol) (RS)-6-(4-methyl-piperazin-1-yl)-4-o-tolyl-4,5-dihydro-pyridine-3-carboxylic acid methylamide in 15 ml $CHCl_3$ was treated with 2.3 g (23.0 mmol) $MnO_2$. The black suspension was heated to 65° C., stirred for 3 h at 65° C. and treated again with 2.3 g (23.0 mmol) $MnO_2$, stirred for 3 h and added an other 0.9 g (9.2 mmol) $MnO_2$. The reaction mixture was stirred for 10.5 h at 65° C., treated with 0.9 g (9.2 mmol) $MnO_2$, stirred for 1 h at 65° C. and cooled to r.t. After filtration of the $MnO_2$ the solvent was removed under reduced pressure and the residue purified by chromatography over silica gel ($CHCl_3$:MeOH= 4:1) to yield 1.24 g (83.2%) product as a beige foam.

MS (ISP): m/e=326 (18), 325 ([M+H$^+$] 100), 268 (31).

d) 6-Chloro-N-methyl-4-o-tolyl-nicotinamide

A solution of 1.5 g (8.8 mmol) 6-chloro-N-methyl-nicotinamide in 18 ml THF was added at 4° C. over 15 min to a solution of 21.9 ml (21.9 mmol) o-tolylmagnesium chloride 1M in THF. The reaction mixture was stirred at r.t. for 2 h cooled to 4° C. and treated dropwise over 10 min with 30.0 ml 5% aqueous $NH_4Cl$. The aqueous phase was separated and extracted twice with THF and the organic phases were washed twice with 5% aqueous $NH_4Cl$. The combined organic phases were dried over $Na_2SO_4$ and subsequently treated at r.t. in four portions over 10 h with 0.9 g (5.7 mmol) $KMnO_4$. The reaction mixture was stirred for 5.5 h at r.t., filtrated and the solvent was removed. The residue was purified by chromatography over silica gel ($CHCl_3$) to yield 1.8 g (78.9%) product as a yellow oil.

MS (EI): m/e=260 ([M] 12), 245 (17), 230 (100), 194 (18), 166 (32), 139 (27).

e) N-Methyl-6-(4-methyl-piperazin-1-yl)-4-o-tolyl-nicotinamide

A solution of 3.2 g (12.2 mmol) 6-chloro-N-methyl-4-o-tolyl-nicotinamide in 6.7 ml (60.3 mmol)1-methylpiperazine was stirred at 100° C. for 2.5 h. The reaction mixture was cooled to r.t., treated with 10 ml 0.1N NaOH and extracted. The aqueous phase was separated and extracted twice with THF and the organic phases were washed twice with brine. The combined organic phases were dried over $Na_2SO_4$, the solvent was removed under reduced pressure and the residue purified by chromatography over silica gel ($CH_2Cl_2$:MeOH=99:1) to yield 3.3 g (83.7%) product as a beige foam.

MS (EI): m/e=324 ([M] 10), 268 (12), 254 (100).

f) N-(3,5-Bis-trifluoromethyl-benzyl)-N-methyl-6-(4-methyl-piperazin-1-yl)-4-o-tolyl-nicotinamide To a solution of 2.5 g (7.7 mmol) N-methyl-6-(4-methyl-piperazin-1-yl)-4-o-tolyl-nicotinamide in 51 ml THF at 4° C. was added dropwise over 30 min 10.2 ml (10.2 mmol) potassium bis(trimethylsilyl) amide (1M in THF). The reaction mixture was stirred for 30 min and subsequently treated at 4° C. dropwise over 30 min with 1.46 ml (7.7 mmol) 3,5-bis-trifluoromethyl-benzylbromide. The reaction mixture was stirred for 1.5 h at 4° C., treated with 31 ml water and extracted. The aqueous phase was separated and adjusted to pH 12 with 2N NaOH and subsequently extracted with 30 ml ethyl acetate. The aqueous phase was separated, the combined organic phases were dried over $Na_2SO_4$, the solvent was removed under reduced pressure and the residue purified by chromatography over silica gel ($CH_2Cl_2$:MeOH=99:1) to yield 3.6 g (84.1%) product as a beige foam.

MS (ISP): m/e=552 (47), 551 ([M+H$^+$] 100).

EXAMPLE 2

Methyl-[6-(4-methyl-piperazin-1-yl)-4-o-tolyl-pyridin-3-yl]-amine a) 6-Chloro4-o-tolyl-nicotinic acid 13.0 g (82.5 mMol) 6-Chloro-nicotinic acid in 65 ml THF were cooled to 0° C. and 206.3 ml (206.3 mMol) o-tolylmagnesium chloride solution (1M in THF) were added over 45 minutes. The solution obtained was further stirred 3 hours at 0° C. and overnight at room temperature. It was cooled to −60° C. and 103.8 ml (1.8 Mol) acetic acid were added, followed by 35 ml THF and 44.24 g (165 mMol) manganese(III) acetate dihydrate. After 30 minutes at −60° C. and one hour at room temperature, the reaction mixture was filtered and THF removed under reduced pressure. The residue was partitioned between water and dichloromethane and extracted. The crude product was filtered on silica gel (eluent: ethyl acetate/toluene/formic acid 20:75:5) then partitioned between 200 ml aqueous half-saturated sodium carbonate solution and 100 ml dichloromethane. The organic phase was washed with 50 ml aqueous half-saturated sodium carbonate solution. The combined aqueous phases were acidified with 25 ml aqueous HCl 25% and extracted with dichloromethane. The organic extracts were dried ($Na_2SO_4$) and concentrated under reduced pressure to yield 10.4 g (51%) of 6-chloro-4-o-tolyl-nicotinic acid as a yellow foam.

MS (ISN): 246 (M−H, 100), 202 (M—$CO_2H$, 85), 166 (36).

b) 6-Chloro-4-o-tolyl-nicotinamide

To a solution of 8.0 g (32.3 mMol) 6-chloro-4-o-tolyl-nicotinic acid in 48.0 ml THF were added 3.1 ml (42.0 mMol) thionylchloride and 143 □l (1.8 mMol) DMF. After 2 hours at 50° C., the reaction mixture was cooled to room temperature and added to a solution of 72.5 ml aqueous ammonium hydroxide 25% and 96 ml water cooled to 0° C. After 30 minutes at 0° C., THF was removed under reduced pressure and the aqueous layer was extracted with ethyl acetate. Removal of the solvent yielded 7.8 g (98%) 6-chloro-4-o-tolyl-nicotinamide as a beige crystalline foam.

MS (ISP): 247 (M+H$^+$, 100).

c) 6-(4-Methyl-piperazin-1-yl)-4-o-tolyl-nicotinamide 1.0 g (4.05 mMol) 6-Chloro-4-o-tolyl-nicotinamide in 9.0 ml 1-methyl-piperazine was heated to 100° C. for 2 hours. The excess N-methyl-piperazine was removed under high vacuum and the residue was filtered on silica gel (eluent: dichloromethane) to yield 1.2 g (95%) 6-(4-methyl-piperazin-1-yl)-4-o-tolyl-nicotinamide as a light yellow crystalline foam.

MS (ISP): 311 (M+H$^+$, 100), 254 (62).

d) 6-(4-Methyl-piperazin-1-yl)-4-o-tolyl-pyridin-3-ylamine

A solution of 0.2 g (0.6 mMol) 6-(4-methyl-piperazin-1-yl)-4-o-tolyl-nicotinamide in 1.0 ml methanol was added to a solution of 103 mg (2.6 mMol) sodium hydroxide in 1.47 ml (3.2 mMol) NaOCl (13%) and heated for 2 hours at 70° C. After removal of methanol, the aqueous layer was extracted with ethyl acetate. The combined organic extracts were dried ($Na_2SO4$), concentrated under reduced pressure and the residue filtered on silica gel (eluent:dichloromethane/methanol 4:1) to yield 100 mg (70%) 6-(4-methyl-piperazin-1-yl)-4-o-tolyl-pyridin-3-ylamine as a brown resin.

MS (ISP): 283 (M+H$^+$, 100), 226 (42).

e) [6-(4-Methyl-piperazin-1-yl)-4-o-tolyl-pyridin-3-yl]-carbamic acid methyl ester 2.15 ml (11.6 mMol) Sodium methoxide in methanol were added over 30 minutes to a suspension of 0.85 g (4.6 mMol) N-bromosuccinimide in 5.0 ml dichloromethane cooled to −5° C. The reaction mixture was stirred 16 hours at −5° C. Still at this temperature, a solution of 1.0 g (3.1 mMol) 6-(4-methyl-piperazin-1-yl)-4-o-tolyl-nicotinamide in 5.0 ml methanol was added over 20 minutes and stirred for 5 hours. 7.1 ml (7.1 mMol) Aqueous HCl 1N and 20 ml dichloromethane were added. The phases were separated and the organic phase was washed with deionized water. The aqueous phases were extracted with dichloromethane, brought to pH=8 with aqueous NaOH 1N and further extracted with dichloromethane. The latter organic extracts were combined, dried ($Na_2SO_4$) and concentrated to yield 1.08 g (quant.) [6-(4-methyl-piperazin-1-yl)-4-o-tolyl-pyridin-3-yl]-carbamic acid methyl ester as a grey foam.

MS (ISP): 341 (M+H$^+$, 100), 284 (35).

f) Methyl-[6-(4-methyl-piperazin-1-yl)-4-o-tolyl-pyridin-3-yl]-amine

A solution of 0.5 g (1.4 mMol) [6-(4-methyl-piperazin-1-yl)-4-o-tolyl-pyridin-3-yl]-carbamic acid methyl ester in 3.0 ml dichloromethane was added over 10 minutes to a solution of 1.98 ml (6.9 mMol) Red-Al® (70% in toluene) and 2.5 ml toluene (exothermic, cool with a water bath to avoid temperature to go >50° C.). The reaction mixture was stirred 2 hours at 50° C., cooled to 0° C., and 4 ml aqueous NaOH 1N were carefully (exothermic) added over 15 minutes, followed by 20 ml ethyl acetate. The phases were separated and the aqueous phase was extracted with ethyl acetate. The combined organic extracts were washed with deionized water and brine, dried ($Na_2SO_4$) and concentrated under reduced pressure to yield 0.37 g (89%) methyl-[6-(4-methyl-piperazin-1-yl)-4-o-tolyl-pyridin-3-yl]-amine as an orange resin.

MS (ISP): 297 (M+H$^+$, 100).
Alternatively 35 g (124 mMol) 6-(4-Methyl-piperazin-1-yl)-4-o-tolyl-pyridin-3-ylamine were dissolved in 273 ml ortho-formic acid trimethyl ester and 8 drops trifluoroacetic acid were added. The reaction mixture was refluxed for 3 hours then concentrated under reduced pressure and dried under high vacuum. The residue was dissolved in 100 ml tetrahydrofuran and added dropwise at 0° C. to a suspension of 9.4 g (248 mMol) lithium alimunium hydride in 300 ml tetrahydrofuran. The reaction mixture was stirred at room temperature for 1 hour, cooled again to 0° C. and its pH was brought to 1 by careful addition of aqueous HCl 28%. After 5 minutes, the pH was raised to 10 by addition of aqueous NaOH 28%, the reaction mixture was filtered on Hyflo and concentrated under reduced pressure. The residue was chromatographed (eluent: dichloromethane/methanol 9:1) to yield 23.6 g (64%) methyl-[6-(4-methyl-piperazin-1-yl)-4-o-tolyl-pyridin-3-yl]-amine as a brown oil.

MS (ISP): 297 (M+H$^+$, 100).

EXAMPLE 3

N-Benzyl-6-morpholin-4-yl-4-o-tolyl-nicotinamide a) N-Benzyl-6-chloro-nicotinamide 3.5 ml (47.6 mMol) Thionylchloride and 50 □l DMF were added to a suspension of 5.0 g (31.7 mMol) 6-chloronicotinic acid in 50 ml toluene and the reaction mixture was heated at 80° C. for 2 hours. The solvent and excess thionyl chloride were removed under reduced pressure and the residue was dissolved in 50 ml dichloromethane. After cooling to 0° C., 10.4 ml (95.2 mMol) benzylamine were added over 20 minutes and after 30 minutes further stirring at room temperature, the reaction mixture was poured onto 50 ml aqueous saturated sodium bicarbonate solution. Extraction with dichloromethane, followed by crystallization from ethyl acetate/n-hexane 2:1 gave 6.13 g (78%) N-benzyl-6-chloro-nicotinamide as light brown crystals of m.p.=113–114° C.

MS (EI): 246 (M$^+$, 100), 211 (M$^+$—Cl, 19), 140 (M$^+$—NHBn, 64).

b) N-Benzyl-6-chloro-4-o-tolyl-nicotinamide

A solution of 0.5 g (2.0 mMol) N-benzyl-6-chloro-nicotinamide in 5.0 ml THF was added over 25 minutes to 10.1 ml (10.1 mMol) of o-tolylmagnesium chloride solution (1M in THF) cooled to 0° C. After 2.5 hours stirring at room temperature, the reaction mixture was cooled again to 0° C. and 4.0 ml acetic acid were added over 15 minutes followed by 1.1 g (4.1 mMol) manganese triacetate dihydrate. After stirring for 1 hour at room temperature, the reaction mixture was filtered and the filtrate was poured onto 20 ml deionized water. Sodium bicarbonate was added portionwise to bring the pH to 7 and the phases were separated. The aqueous layer was extracted with dichloromethane. The combined organic extracts were washed with water, dried ($Na_2SO_4$) and evaporated. The residue was purified by flash chromatography (eluent ethyl acetate/n-hexane 2:1) to yield 0.6 g (88%) N-benzyl-6-chloro-4-o-tolyl-nicotinamide as an orange resin.

MS (EI): 336 (M$^+$, 49), 230 (M$^+$—PhNH, 100), 106 (75), 91 (82).

c) N-Benzyl-6-morpholin-4-yl-4-o-tolyl-nicotinamide

A mixture of 5.0 g (14.8 mMol) of N-benzyl-6-chloro-4-o-tolyl-nicotinamide and 25 ml morpholine was heated to 100° C. for 3.5 hours. After cooling to room temperature, extractive work-up with ethyl acetate, water and brine gave 5.7 g (100%) N-benzyl-6-morpholin-4-yl-4-o-tolyl-nicotinamide as a yellow powder.

MS (ISP): 388 (M+H$^+$, 100).

EXAMPLE 4

2-(3,5-Bis-trifluoromethyl-phenyl)-N-methyl-N-(6-morpholin-4-yl-4-o-tolyl-pyridin-3-yl)-isobutyramide a) N-tert.-Butyl-6-chloro-nicotinamide 25.7 ml (349 mMol) Thionylchloride and 0.5 ml (6.35 mMol) DMF were added to a suspension of 50.0 g (317 mMol) 6-chloro-nicotinic acid in 250 ml toluene and the reaction mixture was heated to 80° C. for 2 hours. After cooling to 10° C., 100.5 ml (952 mMol) tert.-butylamine were added over 40 minutes and stirring was pursued for 30 minutes at the same temperature. 250 ml Aqueous sodium hydroxide 2N were added and the mixture was stirred 30 minutes at room temperature. Dilution with 300 ml water and extraction with ethyl acetate yielded 63.3 g (94%) N-tert.-butyl-6-chloro-nicotinamide as a beige powder of m.p.=108–110° C.

MS (ISP): 235 (M+Na$^+$, 36), 213 (M+H$^+$, 100), 157 (M—$C_4H_8$, 25).

b) N-tert.-Butyl-6-chloro-4-o-tolyl-nicotinamide 92 ml (92 mMol) o-Tolylmagnesium chloride solution (1M in THF) were added over 15 minutes to a solution of 5.0 g (23 mMol) N-tert.-butyl-6-chloro-nicotinamide in 25 ml THF cooled to 0° C. The reaction mixture was stirred 18 hours at 30° C. and cooled again to 0° C. 5.6 ml (138 mMol) Methanol were added over 30 minutes, stirring was pursued for 10 minutes and 6.3 g (27 mMol) 2,3-dichloro-5,6-dicyano-1,4-benzoquinone were added. After 1 hour at room temperature, the reaction mixture was concentrated to 50 g under reduced pressure, heated to 50° C. and 100 ml tert.-butyl-methylether were added. The resulting suspension was refluxed for 30 minutes, cooled to room temperature and, after 1 hour, filtered off. The filtrate was concentrated and dried under high vacuum to yield 6.3 g (90%) of N-tert.-butyl-6-chloro-4-o-tolyl-nicotinamide as an orange foam.

MS (ISP): 303 (M+H$^+$, 100), 247 (M—$C_4H_8$, 10).
Alternatively

To a solution of 3-N-tert-Butyl-6-chloro-nicotinamide (10.0 g, 47.0 mmol) in THF (50 ml) at 2–4° C. was added a solution of o-tolylmagnesium chloride (1.0 M solution in THF, 190 ml, 188.10 mmol, 4.0 eq) dropwise over 30 minutes and the resulting suspension warmed to 30° C. for 18 h. The obtained brown solution was cooled to 0–4° C. and MeOH (11.43 ml, 282.10 mmol, 6 eq) added dropwise over 20 min followed by o-chloranil (15.34 g, 61.13 mmol, 1.3 eq.) The dark green solution was stirred at 22° C. for one hour and then concentrated to give 71.71 g of a blue foam. This was taken up in MeOH (200 ml) and $H_2O$ (75 ml), stirred for 30 min and filtered through Speedex, the filtrate concentrated, suspended between TBME and 1 N NaOH, stirred for 12 h and again filtered through Speedex. The organic phase was washed with aq $NaHCO_3$, $H_2O$ and brine, dried over $MgSO_4$ and concentrated to give 13.57 g brown solid which was recrystallised from heptane (100 ml) to give 6.94 g of product (93% pure by quantitative hplc) as a yellow solid m.p. 120° C.; IR (NJL): 3305m (NH), 1637s (C=O); MS(EI): 303 ([M+H]$^+$); 1H NMR (DMSO): 1.06 (s, 9H), 2.10 (s, 3H), 7.18–7.32 (m, 4H), 7.45 (s, 1H), 7.61 (bs, 1H), 8.46 (s, 1H). The residue from the above recrystallisation was continuously extracted with TBME for 16 h and combined with the mother liquor, concentrated and recrystallised three times from heptane to give a further 0.71 g of product (91% pure by quant. hplc). Total yield: 54%.

c) N-tert.-Butyl-6-morpholin-4-yl-4-o-tolyl-nicotinamide

A mixture of 6.0 g (19 mMol) of N-tert.-butyl-6-chloro-4-o-tolyl-nicotinamide and 12 ml (138 mMol) morpholine was heated at 100° C. for 4 hours. After cooling to room temperature, extractive work-up with ethyl acetate, water and brine yielded 6.3 g (91%) of N-tert.-butyl-6-morpholin-4-yl-4-o-tolyl-nicotinamide as a brown crystalline foam.

MS (ISP): 376 (M+Na$^+$, 8), 354 (M+H$^+$, 100).
Alternatively 92 ml (92 mMol) o-Tolylmagnesium chloride solution (1M in THF) were added over 15 minutes to a solution of 5.0 g (23 mMol) N-tert.-butyl-6-chloro-nicotinamide in 25 ml THF cooled to 0° C. The reaction mixture was stirred 18 hours at 30° C and cooled again to 0° C. 5.6 ml (138 mMol) Methanol were added over 30 minutes, stirring was continued for 10 minutes and 6.2 g (25 mMol) o-chloranil were added. After 30 minutes at room temperature, the green solution was concentrated under reduced pressure to a green-black foam. This residue was suspended in 48.8 ml morpholine and stirred at 100° C. for 30 minutes. After cooling to 50° C., 100 ml tert.-butyl-methylether were added and the suspension further cooled to room temperature. After 30 minutes at room temperature, it was filtered, the precipitate was washed with tert.-butyl-methylether and the filtrate was poured onto 50 ml aqueous NaOH 1N. The phases were separated and the aqueous phase was extracted with tert.-butyl-methylether. The combined organic extracts were washed with deionized water and brine, dried ($Na_2SO_4$) and concentrated under reduced pressure to yield 6.2 g (75%) N-tert.-butyl-6-morpholin-4-yl-4-o-tolyl-nicotinamide as a brown resin.

MS (ISP): 376 (M+Na$^+$, 6), 354 (M+H$^+$, 100)

d) 6-Morpholin-4-yl-4-o-tolyl-nicotinamide

A mixture of 6.0 g (16.5 mMol) N-tert.-butyl-6-morpholin-4-yl-4-o-tolyl-nicotinamide and 12 ml (185 mMol) methanesulfonic acid was stirred at 100° C. for 5 hours, then poured on ice. The aqueous phase was extracted with tert.-butyl-methylether, brought to pH=10 with NaOH aq. 28% and extracted further with tert.-butyl-methylether. The second organic extracts were dried ($Na_2SO_4$) and concentrated to yield 4.75 g (96%) 6-morpholin-4-yl-4-o-tolyl-nicotinamide as a light beige crystalline foam.

MS (ISP): 320 (M+Na$^+$, 5), 298 (M+H$^+$, 100).
Alternatively 0.5 g (1.29 mMol) N-Benzyl-6-morpholin-4-yl-4-o-tolyl-nicotinamide was dissolved in 2.5 ml methanesulfonic acid and 0.25 ml sulfuric acid and heated to 100° C. for 1 hour. A second portion of 0.25 ml sulfuric acid was added and heating was pursued for 22 hours. After cooling to room temperature, the reaction mixture was poured onto 75 ml aqueous saturated sodium carbonate, cooled with ice and extracted with ethyl acetate. The combined organic extracts were washed with aqueous saturated sodium carbonate and brine, dried ($Na_2SO_4$) and concentrated. The residue was flash chromatographed (eluent: dichloromethane/methanol 95:5) to yield 0.15 g (39%) 6-morpholin-4-y1-4-o-tolyl-nicotinamide as a yellow resin.

MS (EI): 297 (M$^+$, 73), 266 (100), 252 (44), 240 (72).

e) (6-Morpholin-4-yl4-o-tolyl-pyridin-3-yl)-carbamic acid methyl ester 9.9 ml (53.7 mMol) Sodium methoxide solution (5.4 M in MeOH) were added over 15 minutes to a solution of 3.9 g (21.5 mMol) N-bromosuccinimide in 22.5 ml dichloromethane cooled to −5° C. The milky suspension was stirred at −5° C. for 18 hours, then, at the same temperature, a solution of 4.5 g (14 mMol) 6-morpholin-4-yl-4-o-tolyl-nicotinamide in 22.5 ml dichloromethane was added over 15 minutes. After 5 hours at −5° C., 33 ml (33 mMol) aqueous HCl 1N were added, the phases were separated, the organic phase washed with water and the aqueous phases extracted with dichloromethane. The combined organic phases were dried ($Na_2SO_4$) and evaporated. The residue was treated with basic Alox (1:1 weight) in ethyl acetate/heptane 1:1 for 30 minutes at room temperature. After filtration and removal of the solvents, the residue was crystallized from di-isopropylether/n-heptane 1:2 at 0° C. to yield 3.4 g (72.5%) (6-morpholin-4-yl-4-o-tolyl-pyridin-3-yl)-carbamic acid methyl ester as a yellow powder.

MS (ISP): 350 (M+Na$^+$, 3), 328 (M+H$^+$, 100), 296 (M—MeO, 13).

Alternatively: MS (ISP): 359 (M+Na$^+$, 4), 328 (M+H$^+$, 100), 296 (M—MeO, 13).

f) Methyl-(6-morpholin-4-yl-4-o-tolyl-pyridin-3-yl)-amine

A solution of 3.0 g (9.1 mMol) (6-morpholin-4-yl-4-o-tolyl-pyridin-3-yl)-carbamic acid methyl ester in 15 ml toluene was added at room temperature over 15 minutes to a solution of 13 ml (46 mMol) Red-Al® (70% in toluene) and 15 ml toluene. After 2 hours at 50° C., the reaction mixture was cooled to 0° C. and 25.5 ml aqueous NaOH 1N were added over 10 minutes (very exothermic). The phases were separated and the aqueous phase extracted with toluene. The combined organic extracts were washed with water and brine, dried ($Na_2SO_4$) and evaporated. The residue was crystallized from n-heptane at −10° C. to yield 2.3 g (88%) methyl-(6-morpholin-4-yl-4-o-tolyl-pyridin-3-yl)-amine as a light beige powder of m.p.=73.5–76° C.

MS (ISP): 284 (M+H$^+$, 100).

g) 2-(3,5-Bis-trifluoromethyl-phenyl)-N-methyl-N-(6-morpholin-4-yl-4-o-tolyl-pyridin-3-yl)-isobutyramide A solution of 11.8 g (36.9 mMol) 2-(3,5-bis-trifluoromethyl-phenyl)-2-methyl-propionyl chloride and 50 ml dichloromethane was added dropwise over 15 minutes at 0° C. to a solution of 10.0 g (34.5 mMol) methyl-(6-morpholin-4-yl-4-o-tolyl-pyridin-3-yl)-amine and 8.30 ml (48 mMol) N-ethyl-di-isopropylamine in 70 ml dichloromethane. The reaction mixture was stirred 3.0 hours at 0° C., poured onto 80 ml deionized water and stirred further 30 minutes at room temperature. The phases were separated and the aqueous phase extracted with dichloromethane. The organic extracts were washed with deionized water, aqueous sodium hydroxide 2% and aqueous sodium bicarbonate 5%, dried ($Na_2SO_4$) and concentrated under reduced pressure. The residue was crystallized from ethanol at −20° C. to yield 16.25 g (81%) 2-(3,5-bis-trifluoromethyl-phenyl)-N-methyl-N-(6-morpholin-4-yl-4-o-tolyl-pyridin-3-yl)-isobutyramide as a white powder. m.p.=128.8–129.9° C. Concentration of the mother-liquors gave 4.4 g of a slowly crystallizing orange oil which can be further purified.

MS (ISP): 588 ($M+Na^+$, 9), 566 ($M+H^+$, 100).

EXAMPLE 5

6-Chloro-N,N-diethyl)4-o-tolyl)-nicotinamide a) 6-Chloro-N,N-diethyl-nicotinamide 0.51 ml (6.98 mMol) Thionylchloride and 10 □l DMF were added to a suspension of 1.0 g (6.34 mMol) 6-chloronicotinic acid in 5 ml tetrahydrofuran. The reaction mixture was stirred at 65° C. for 1.5 hours, cooled to 0° C. and 1.98 ml (19.0 mMol) diethylamine were added over 40 minutes. The resulting suspension was stirred 4 hours at room temperature and 1 hour at 60° C. After cooling to room temperature, 5.0 ml aqueous NaOH 2N were added and stirring pursued for 30 minutes. The system was diluted with 25 ml deionized water and 20 ml ethyl acetate. The phases were separated and the aqueous phase was further extracted with ethyl acetate. The combined organic extracts were washed with aqueous NaOH 1N and half-saturated aqueous NaCl, dried ($Na_2SO_4$) and evaporated to yield 0.68 g (50%) 6-chloro- N,N-diethyl-nicotinamide as a yellow oil.

MS (ISP): 425 ($2M+H^+$, 82), 230 ($M+NH_4^+$, 62), 213 ($M+H^+$, 100).

b) 6-Chloro-N,N-diethyl-4-o-tolyl-nicotinamide 7.62 ml (7.62 mMol) o-Tolylmagnesium chloride solution (1M in THF) were added over 15 minutes to a solution of 0.60 g (2.54 mMol) 6-chloro- N,N-diethyl-nicotinamide in 3.0 ml THF cooled to 0° C. The reaction mixture was stirred 2 hours at room temperature, then cooled again to 0° C. and 0.41 ml methanol (10.1 mMol) were added followed by 692 mg 2,3-dichloro-5,6-dicyano-1,4-benzoquinone (3.1 mMol). After stirring 2 hours at room temperature, the reaction mixture was concentrated under reduced pressure and 50 ml t-butyl-methylether were added at 50° C. The resulting suspension was filtered off, the filtrate was concentrated and the residue was purified by flash chromatography (eluent: ethyl acetate/n-heptane 1:1) to yield 0.67 g (86%) of 6-chloro-N,N-diethyl-4-o-tolyl-nicotinamide as a yellow oil.

MS (EI): 301 (M−H, 10); 267 (M—Cl, 6); 230 (M—$Et_2N$, 100); 166 (31).

EXAMPLE 6

N-tert.-Butyl-6-methyl-4-o-tolyl-nicotinamide a) N-tert.-Butyl-6-methyl-nicotinamide 3.5 ml (40 mMol) Oxalylchloride and 57.4 □l (0.74 mMol) DMF were added to a suspension of 5.0 g (36.5 mMol) 6-methyl-nicotinic acid in 25 ml toluene and the system was heated to 40° C. for one hour. After diluting with 20 ml toluene and cooling to 0° C., 11.5 ml (109 mMol) tert.-butylamine were slowly added. After 30 minutes stirring at room temperature, 25 ml aqueous NaOH 2N were added and stirring pursued for 30 minutes. The phases were separated and the aqueous phase was extracted with toluene. The combined organic extracts were washed with water and brine, dried ($Na_2SO_4$) and concentrated. The residue was purified by flash chromatography (eluent: ethyl acetate/n-heptan 1:1) to yield 5.4 g (77%) N-tert.-butyl-6-methyl-nicotinamide as a light beige solid of m.p. =103.5–104.8° C.

MS (EI): 192 ($M^+$, 22), 177 ($M^+$—$CH_3$, 27), 120 ($M^+$—NHtBu, 100).

b) N-tert.-Butyl-6-meth-4-o-tolyl-nicotinamide 38.9 ml (38.9 mMol) o-Tolylmagnesium chloride solution (1M in THF) were added over 15 minutes to a solution of 2.5 g (10.1 mMol) N-tert.-butyl-6-methyl-nicotinamide in 12.5 ml THF cooled to 0° C. The suspension obtained was stirred overnight at room temperature, then one more hour at 50° C. After cooling to 0° C., 2.1 ml (51.9 mMol) methanol were added over 30 minutes (exothermic!), followed after 10 minutes by 3.5 g (15.6 mMol) 2,3-dichloro-5,6-dicyano-benzoquinone. After one hour at room temperature, the reaction mixture was concentrated under reduced pressure to a still stirrable oil, heated to 50° C. and 100 ml tert.-butyl-methylether were added. The suspension was stirred 30 minutes at reflux, 1 hour at room temperature and filtered. The filtrate was evaporated and the residue was purified by flash chromatography (50 g $SiO_2$, eluent: AcOEt/n-heptane 2:1) to yield 3.1 g (84.5%) N-tert.-butyl-6-methyl-4-o-tolyl-nicotinamide as a light brown resinous solid.

MS (EI): 282 ($M^+$, 11), 210 ($M^+$—NHtBu, 100).

EXAMPLE 7

N-tert-Butyl1-6-chloro-4-(prop-2-yl)-nicotinamide 7.0 ml (14.1 mMol) iso-Propylmagnesium chloride solution (2M in THF) were added over 5 minutes to a solution of 1.0 g (4.7 mMol) N-tert.-butyl-6-chloro-nicotinamide in 5.0 ml THF cooled to 0° C. and the reaction mixture was stirred 18 hours at room temperature. After cooling to 0° C., 1.14 ml (28.2 mMol) methanol were added over 10 minutes, followed, after 15 minutes, by 1.17 g (5.2 mMol) 2,3-dichloro-5,6-dicyano-1,4-benzoquinone. After stirring 30 minutes at room temperature, the red-brown solution was concentrated under reduced pressure to about 10 g, heated to 50° C. and 20 ml tert.-butyl-methylether were added. The resulting suspension was stirred 1 hour at 55° C., then 1 hour at room temperature and filtered. The filtrate was concentrated under reduced pressure and digested in 9 ml n-hexane/ethyl acetate 4:1 to yield 0.67 g (56%) N-tert.-butyl-6-chloro-4-(prop-2-yl)-nicotinamide as a beige powder of m.p.=130–140° C. (dec.)

MS (EI): 254 ($M^+$, 51), 198 ($M^+$—$C_4H_8$, 38), 182 ($M^+$—NHtBu, 100).

EXAMPLE 8

N-tert.-Butyl-6-chloro-4-p-fluorophenyl-nicotinamide 14.1 ml (14.1 mMol) 4-Fluoro-phenylmagnesium chloride solution (1M in THF) were added over 10 minutes to a solution of 1.0 g (4.7 mMol) N-tert.-butyl-6-chloro-nicotinamide in 5.0 ml THF cooled to 0° C. and the reaction mixture was stirred 18 hours at 35° C. After cooling to 0° C., 1.14 ml (28.2 mMol) methanol were added over 20 minutes, followed, after 15 minutes, by 1.17 g (5.2 mMol) 2,3-dichloro-5,6-dicyano-1,4-benzoquinone. After 30 minutes at room temperature, the brown solution was concentrated under reduced pressure to about 10 g, heated to 50° C. and 20 ml tert.-butyl-methylether were added. The resulting suspension was stirred 1 hour at 55° C., then 1 hour at room temperature and filtered. The filtrate was concentrated under reduced pressure and digested in 5 ml n-hexane/ethyl acetate 4:1 to yield 0.69 g (48%) N-tert.-butyl-6-chloro-4-p-fluoro-phenyl-nicotinamide as a light brown powder of m.p.= 168–173° C.

MS (ISP): 307 (M+H$^+$, 100).

What is claimed is:

1. A process for preparing a compound of formula

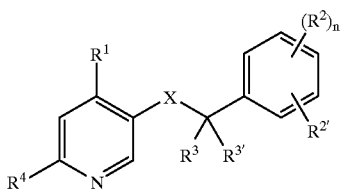

I wherein $R^1$ is lower alkyl or aryl, optionally substituted by lower alkyl, lower alkoxy, halogen or trifluoromethyl;

$R^2$ and $R^{2'}$ are independently from each other hydrogen, halogen, trifluoromethyl, lower alkoxy or cyano; or $R^2$ and $R^{2'}$ may together be —CH=CH—CH=CH— and form a fused ring with the carbon atoms to which they are attached, optionally substituted by lower alkyl or lower alkoxy;

$R^3/R^{3'}$ are independently from each other hydrogen, lower alkyl, or taken together with the carbon atom to which they are attached, form a cycloalkyl group;

$R^4$ is hydrogen, lower alkyl, —N($R^5$)$_2$, —N($R^5$)(CH$_2$)$_n$OH, —N($R^5$)S(O)$_2$-phenyl, —N($R^5$)S(O)$_2$-lower alkyl, —N=CH—N($R^5$)$_2$, —N($R^5$)C(O)$R^5$ or a cyclic tertiary amine of the group

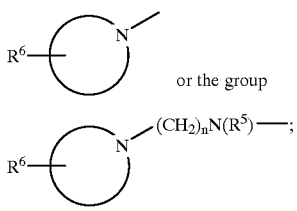

$R^5$ is hydrogen, lower alkyl, or benzyl, which is optionally substituted by lower alkyl;

$R^6$ is hydrogen, hydroxy, lower alkyl, —(CH$_2$)$_n$COO-lower alkyl, —N($R^5$)CO-lower alkyl, hydroxy-lower alkyl, cyano, —(CH$_2$)$_n$O(CH$_2$)$_n$OH, —CHO, or a 5- or 6 membered heterocyclic ring, optionally bonded via an alkylene group, X is —C(O)N($R^5$)— or —N($R^5$)C(O)—;

n is 0–4; and pharmaceutically acceptable acid addition salts thereof, which process comprises a) reacting a compound of formula

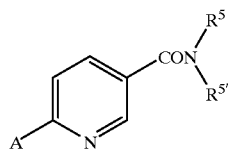

IV-1 wherein A denotes R or $R^4$, and R is halogen, and $R^{5'}$ has the same meaning as $R^5$, wherein $R^5$ and $R^{5'}$ may be independent from each other, with a compound of formula R$^1$MgHal V wherein Hal is a halogen atom, to a mixture of compounds of formulae

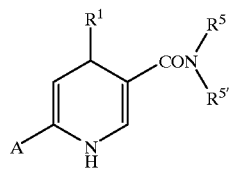

X-1 and

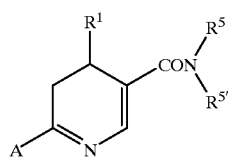

XI-1 or a') reacting a compound of formula IV-1, wherein A is R, with a compound of formula V and with a compound of formula

HR$^4$ VII in one reaction step, to a compound of formula

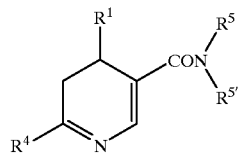

VI and b) oxidizing a compound of formulae X-1, XI-1 or VI with an oxidizing agent, to a compound of formula

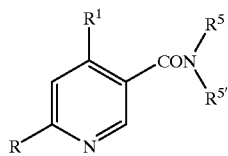
XII or

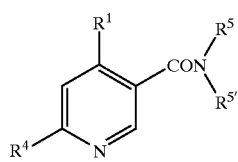
VIII and c) reacting a compound of formula VIII with a compound of formula

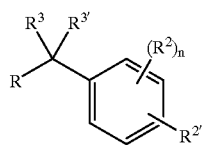
IX wherein R is halogen, to a compound of formula

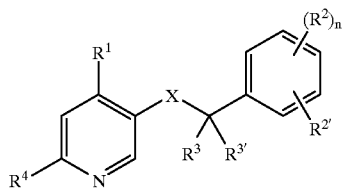
I wherein X is —CON(R$^5$)—, or c'i) reacting a compound of formula VIII with a compound of formula IX, to a compound of formula

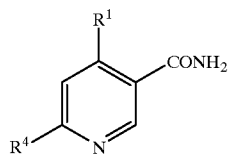
XIII and ii) reacting a compound of formula XIII to a compound of formula

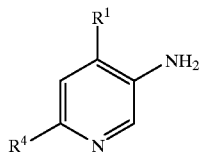
XIV or

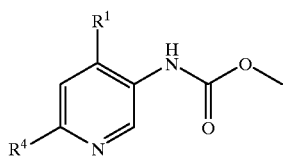
XV and iii) transforming a compound of formulae XIV or XV to a compound of formula

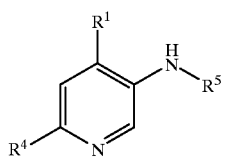
XVI wherein R$^5$ is methyl, and iv) reacting a compound of formula XVI with a compound of formula

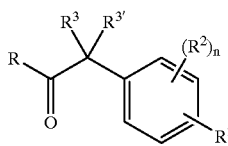
XVII to a compound of formula

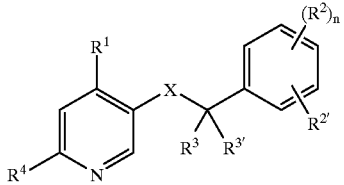
I wherein X is —N(R$^5$)C(O)—.

2. A process in accordance with claim 1, step a), wherein the solvent is THF.

3. A process in accordance with claim 1, step b), wherein the oxidizing agent is selected from the group consisting of Mn(OAc)$_3$, Cu(OAc)$_2$, iodine, bromine, N-bromosuccinimide, Pd/C, Pt/C, DDQ (2,3-dichloro-5,6-dicyano-1,4-benzoquinone), o-chloranil, $H_2O_2$-urea, $Na_2CO_3$—$H_2O_2$, $MnO_2$, $KMnO_4$, $RuCl_2(PPh_3)_3$ Cer(IV) ammoniumnitrate, $HNO_3$ and S.

4. A process in accordance with claim 1, step c), wherein the reaction is carried out in THF and in the presence of potassium bis(trimethylsilyl)amide.

5. A process in accordance with claim 1, wherein the compound of formula I wherein X is —$CON(R^5)$— obtained from step c) is N-(3,5-bis-trifluoromethyl-benzyl)-N-methyl-6-(4-methyl-piperazin-1-yl)-4-o-tolyl-nicotinamide.

6. A process in accordance with claim 1, step c'i), wherein the reaction is carried out in the presence of sulfuric acid and AcOH or methanesulfonic acid.

7. A process in accordance with claim 1, step c'ii), wherein the amino substituent is introduced via a Hofmann rearrangement.

8. A process in accordance with claim 1, step c'iii) for the preparation of a compound of formula XVI starting from a compound of formula XIV, wherein the reaction is carried out with an alkyl orthoformate and a catalytic amount of an acid and with a reducing agent.

9. A process in accordance with claim 8, wherein the alkyl orthoformate is $HC(OCH_3)_3$ and the acid is trifluoro acetic acid.

10. A process in accordance with claim 8, wherein the reducing agent is selected from the group consisting of $LiAlH_4$, $NaBH_4$, $BH_3$-THF and Red-Al®.

11. A process in accordance with claim 1, step c'iii) for the preparation of a compound of formula XVI starting from a compound of formula XV, wherein the reduction is carried out with a reducing agent selected from the group consisting of $LiAlH_4$ and Red-Al®.

12. A process in accordance with claim 1, step c'iv), wherein the reaction is carried out in the presence of a tertiary amine.

13. A process in accordance with claim 1, step c'iv), wherein the obtained compound of formula I wherein X is —$N(R^5)C(O)$— is 2-(3,5-bis-trifluoromethyl-phenyl)-N-methyl-N-(6-morpholin-4-yl-4-o-tolyl-pyridin-3-yl)-isobutyramide.

14. A process according to claim 1, further comprising reacting a compound of formula XII with a compound of formula VII, to a compound of formula VIII.

* * * * *